(12) United States Patent
Hashimoto et al.

(10) Patent No.: US 10,123,915 B2
(45) Date of Patent: Nov. 13, 2018

(54) DISPOSABLE PULL-ON DIAPER

(71) Applicant: UNICHARM CORPORATION, Shikokuchuo-shi, Ehime (JP)

(72) Inventors: Tatsuya Hashimoto, Kanonji (JP); Jun Fukasawa, Kanonji (JP); Tetsuo Okubo, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 362 days.

(21) Appl. No.: 14/772,776

(22) PCT Filed: Jun. 5, 2013

(86) PCT No.: PCT/JP2013/065630
§ 371 (c)(1),
(2) Date: Sep. 4, 2015

(87) PCT Pub. No.: WO2014/136281
PCT Pub. Date: Sep. 12, 2014

(65) Prior Publication Data
US 2016/0015575 A1 Jan. 21, 2016

(30) Foreign Application Priority Data

Mar. 8, 2013 (JP) ................................. 2013-047393
Jun. 5, 2013 (JP) ................................. 2013-119222

(51) Int. Cl.
*A61F 13/49* (2006.01)
*A61F 13/494* (2006.01)
*A61F 13/496* (2006.01)

(52) U.S. Cl.
CPC ...... *A61F 13/49406* (2013.01); *A61F 13/496* (2013.01); *A61F 13/49017* (2013.01);
(Continued)

(58) Field of Classification Search
CPC .......... A61F 13/49406; A61F 13/49413; A61F 13/4942; A61F 13/49017; A61F 13/49058;
(Continued)

(56) References Cited

U.S. PATENT DOCUMENTS 4,795,454 A * 1/1989 Dragoo ............. A61F 13/49009
604/378
5,911,713 A * 6/1999 Yamada ............ A61F 13/49009
604/385.29
(Continued)

FOREIGN PATENT DOCUMENTS

EP 0951890 A2 10/1999
EP 0951890 A3 8/2001
(Continued)

OTHER PUBLICATIONS

International Search Report dated Jul. 2, 2013 in International Application No. PCT/JP2013/065630.
Extended European Search Report in EP Application No. 13877018.5, dated Feb. 23, 2016.

*Primary Examiner* — Lynne Anderson
(74) *Attorney, Agent, or Firm* — Hauptman Ham, LLP

(57) ABSTRACT

The present invention aims to provide a disposable pull-on diaper improved so that the diaper may be conveniently put on the wearer's body. Each of leg side flaps of a crotch panel has an outer side region and an inner side region. In the lowest region of the crotch region, the outer side region and the inner side region respectively have a dimension of at least 10 mm in a transverse direction wherein the inner side region extends in a longitudinal direction and the outer side region extends in the transverse direction from the inner side region.

10 Claims, 8 Drawing Sheets

(52) U.S. Cl.
CPC .... *A61F 13/49019* (2013.01); *A61F 13/4942* (2013.01); *A61F 13/49058* (2013.01); *A61F 2013/4948* (2013.01); *A61F 2013/49092* (2013.01)

(58) Field of Classification Search
CPC .. A61F 2013/49088; A61F 2013/49092; A61F 2013/49093; A61F 2013/49095; A61F 2013/4944; A61F 2013/4948
See application file for complete search history.

(56) References Cited

U.S. PATENT DOCUMENTS

| | | | | |
|---|---|---|---|---|
| 5,993,433 | A | * | 11/1999 | St. Louis ............ A61F 13/4942 604/385.27 |
| 7,704,243 | B2 | * | 4/2010 | Chang ............... A61F 13/15593 604/385.24 |

FOREIGN PATENT DOCUMENTS

| | | |
|---|---|---|
| EP | 2520259 A1 | 11/2012 |
| EP | 2556809 A1 | 2/2013 |
| JP | 4-144558 A | 5/1992 |
| JP | 4-244152 A | 9/1992 |
| JP | 5-184622 A | 7/1993 |
| JP | 2002-209938 A | 7/2002 |
| JP | 2008-508082 A | 3/2008 |
| JP | 2011-110317 A | 6/2011 |

\* cited by examiner

DISPOSABLE PULL-ON DIAPER

RELATED APPLICATIONS

The present application is a National Phase of International Application Number PCT/JP2013/065630, filed Jun. 5, 2013, which claims priority to Japanese Application Numbers 2013-047393, filed Mar. 8, 2013, and 2013-119222, filed Jun. 5, 2013.

TECHNICAL FIELD

The present invention relates to disposable pull-on diapers, more in detail, the disposable pull-on diaper having a front panel defining a front waist region, a rear panel defining a rear waist region and a crotch panel defining a crotch region.

BACKGROUND

Conventionally, disposable pull-on diapers having a front panel, a rear panel and a crotch panel is well known.

For example, JP 2008-508082 A (Patent Literature 1) discloses a disposable pull-on type wearing article of which an example is a disposable pull-on diaper and an example of this disposable pull-on diaper is a disposable pant-shaped diaper. Leg barrier cuffs rise toward the wearer's body as the diaper is put on the wearer's body.

An example of an absorbent article disclosed in JP H4-144558 A (Patent Literature 2) is a disposable pull-on diaper constituted by a longitudinally long main body including an absorbent body and an annular elastic belt. The main body is formed along both side edges with side flaps and, in leg side regions of these side flaps, gather forming elastic members are arranged.

CITATION LIST

Patent Literature

{PTL 1}: JP 2008-508082 A
{PTL 2}: JP H4-144558 A

SUMMARY

Technical Problem

When a mother tries to put such conventional diaper on a body of her baby, the leg barrier cuffs or the side flaps arranged on both side edge portions of the crotch panel may rise on the side edge portions of the absorbent body under contraction of the elastic members arranged in these barrier cuffs and side flaps so as to straiten the leg-openings. If the mother tries to pass the legs of her baby through the leg-openings straiten in this manner, there will be a possibility that the toe of the baby may be caught by the barrier cuffs or the side flaps, making it difficult to put the diaper on her baby smoothly and quickly.

An object of the present invention is to provide a disposable pull-on diaper improved so that the diaper may be conveniently put on the wearer's body.

Solution to Problem

In order to solve the problem set forth above, the present invention is directed to a disposable pull-on diaper having a longitudinal direction, a transverse direction and a front-back direction wherein side edge portions opposed to each other in the transverse direction of a front panel defining a front waist region are joined to side edge portions opposed to each other in the transverse direction of a rear panel defining a rear waist region to form an annular waist region and wherein front and rear end portions of a crotch panel extending in the front-back direction to define a crotch region are joined to the front waist region and the rear waist region, respectively.

In this diaper, the present invention is featured as described below. The crotch panel includes an absorbent structure located in a central portion in the transverse direction thereof and a pair of leg side flaps extending along the absorbent structure on both sides in the transverse direction thereof. The leg side flaps are formed of nonwoven fabric sheets extending in the transverse direction from the absorbent structure and a plurality of elastic members secured under tension to the respective nonwoven fabric sheets so as to extend parallel in the front-back direction, each of the leg side flaps has a proximal edge integrated with the absorbent structure and a distal edge defining each of side edges of the crotch panel, an area extending in the transverse direction between the proximal edge and the distal edge is divided into an outer side region including the distal edge and the leg elastic members and an inner side region including the proximal edge. One of the leg elastic members is secured to the distal edge. A dimension in the transverse direction between the outer side region and the inner side region is at least 10 mm in an area extending in the transverse direction across the lowest region in the longitudinal direction, the inner side region extends upward in the longitudinal direction from the proximal edge and the outer side region extends outward in the transverse direction from the proximal edge.

Advantageous Effects of Invention

According to one or more embodiments of the present invention, each of the leg side flaps in the crotch region is divided into the outer side region and the inner side region as viewed in the width direction and the respective regions are formed so that the respective regions may have a dimension of at least 10 mm, the inner side region may extend in the longitudinal direction and the outer side region may extend outward in the transverse direction. With the diaper arranged in such manner, the wearer's toe may be caught by the leg side flaps when a mother or a helper tries to pass the baby's legs through the leg openings is drastically alleviated and a convenience to put the diaper on the wearer's body is improved.

DESCRIPTION OF EMBODIMENTS

The disposable pull-on diaper according to the present invention will be described hereunder with reference to the accompanying drawings.

Figure 1:
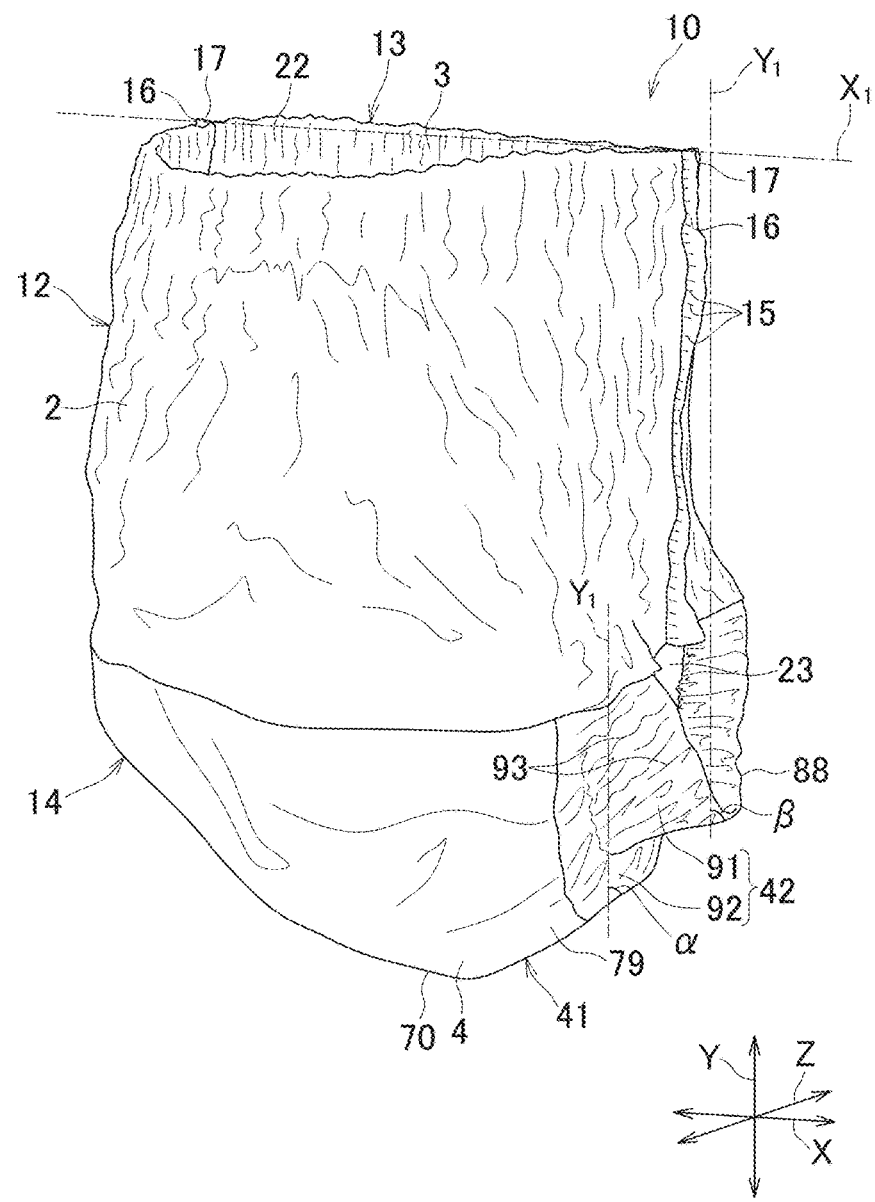
FIG. 1 is a perspective view of a disposable pull-on diaper according to the present invention.

FIG. 1 is a perspective view of a diaper 10 for baby as an example of the disposable pull-on diaper according to the present invention and the diaper 10 is illustrated in a state subjected to no other external force than a force acting to broaden a waist-opening 22 described later. The diaper 10 has a front panel 12 defining a front waist region 2, a rear panel 13 defining a rear waist region 3 and a crotch panel 14 defining a crotch region 4. Side edge portions 16 opposed to each other in a transverse direction X of the front panel 12 and side edge portions 17 opposed to each other in the transverse direction X of the rear panel 13 are put flat and joined together along seams 15 made by ultrasonic joining. The crotch panel 14 has a front end portion 18 and a rear end portion 19, both described later, joined to an interior surface of the front panel 12 and an interior surface of the rear panel 13, respectively. In such diaper 10, the front panel 12 and the rear panel 13 cooperate with each other to form the waist-opening 22 and the front panel 12, the rear panel 13 and the crotch panel 14 cooperate together to form a pair of leg-openings 23. In this regard, only one of leg-openings 23 is illustrated in FIG. 1. Concerning each of the leg-openings 23, a lower portion of a peripheral region is defined by a leg side flap 42 in the crotch panel 14. The leg side flap 42 has an outer side region 91 and inner side region 92 as viewed in the transverse direction X of the diaper 10. In FIG. 1, double-headed arrows X, Y and Z indicate a transverse direction, a longitudinal direction and a front-back direction of the diaper 10.

Figure 2:
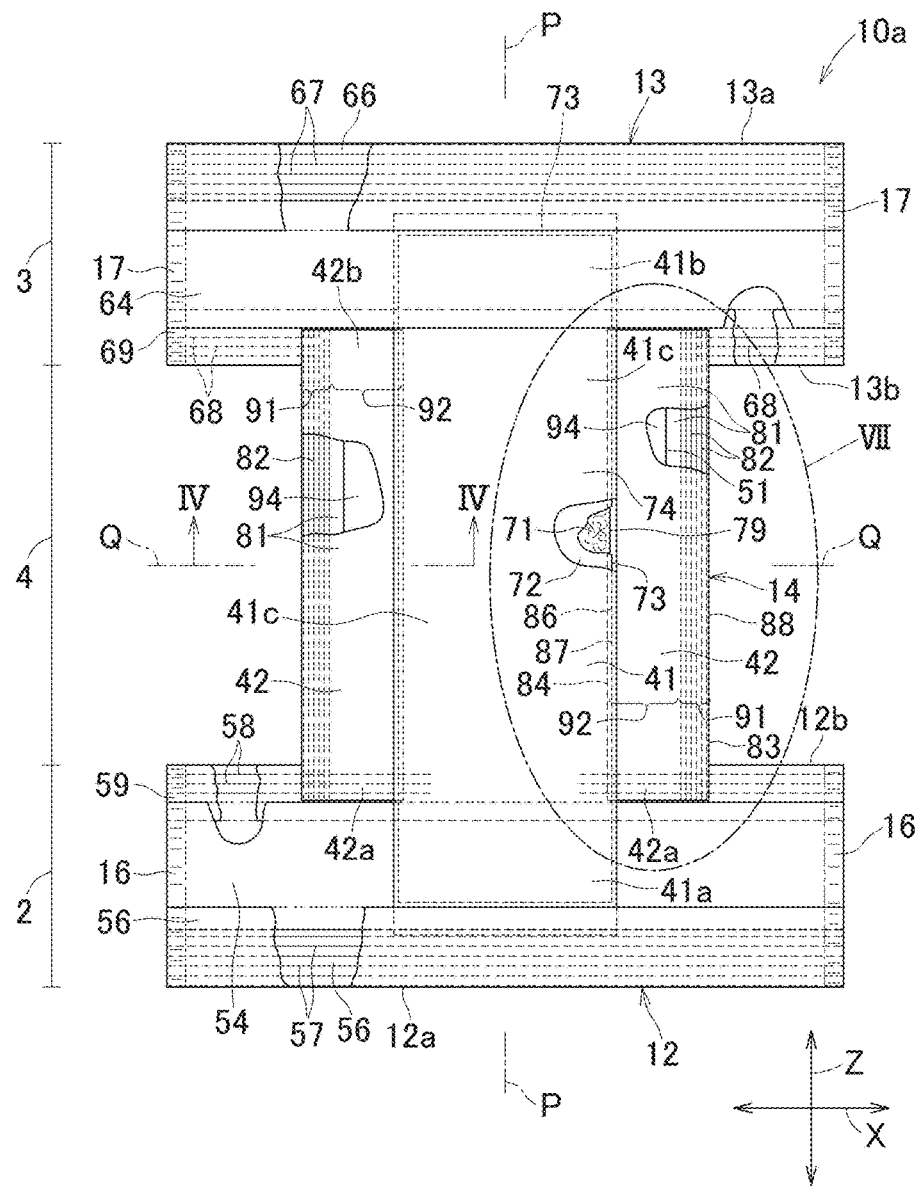
FIG. 2 is an extended plan view of the diaper.
Figure 3:
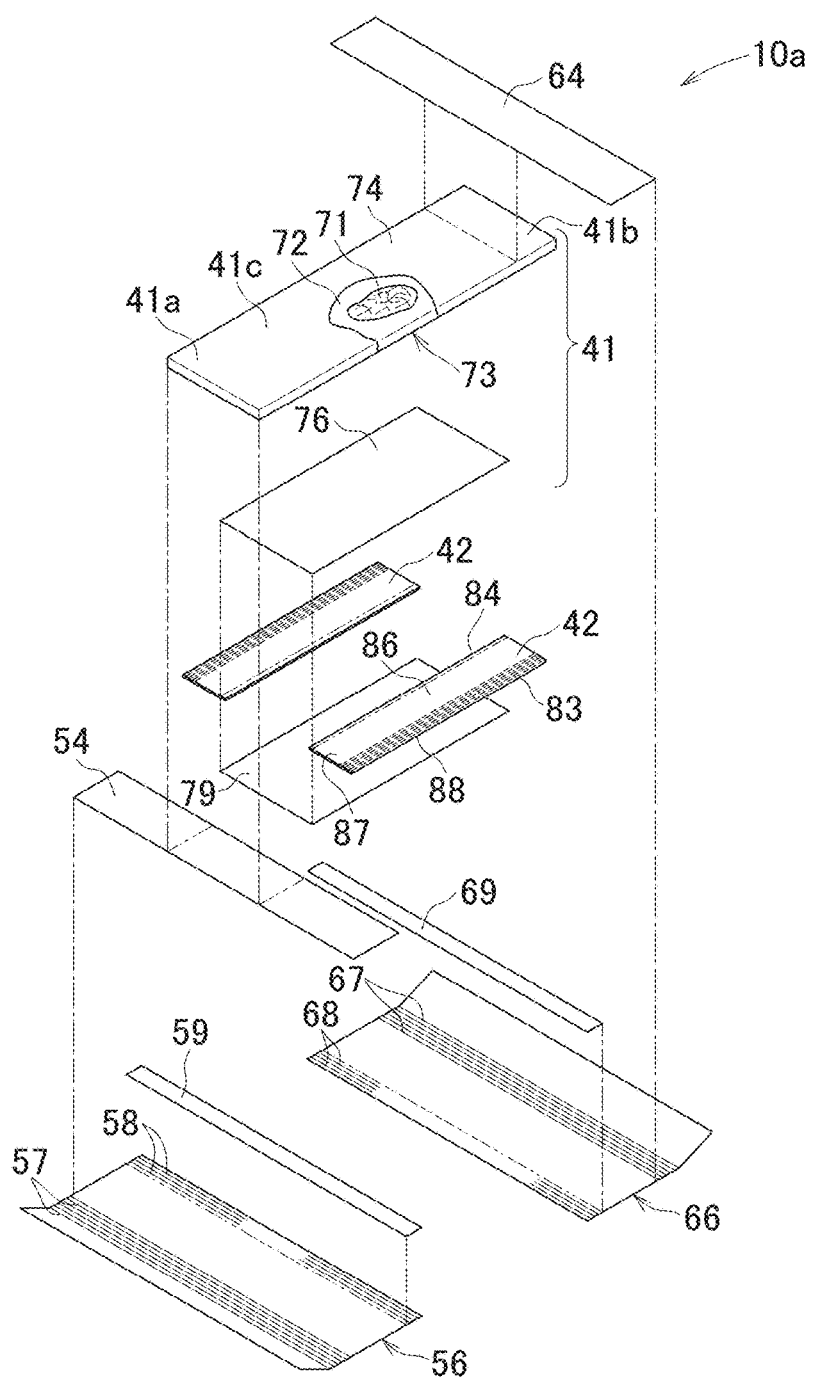
FIG. 3 is an exploded perspective view of the extended diaper.

Of FIGS. 2 and 3, FIG. 2 is a partially cutaway plan view illustrating flatly extended diaper 10a obtained by unjoining the front and rear panels 12, 13 along the seals 15 and extending the front and rear panels 12, 13 and the crotch panel 14 in the transverse direction X and the front-back direction Z, and FIG. 3 is an exploded view of this extended diaper 10a. In these FIGS. 2 and 3, various elastic members described later are under tension in the transverse direction X or in the front-back direction Z. The extended diaper 10a has a longitudinal center line P bisecting a dimension in the transverse direction X and a transverse center line Q bisecting a dimension in the front-back direction Z wherein the extended diaper 10a is made symmetrically about the longitudinal center line P. The term "extended" used herein means that the diaper 10 is whereby or at least partially stretched in the transverse direction X, the longitudinal direction Y or in the front-back direction X until the gathers formed owing to contraction of the elastic members, or traces of folding disappear.

The front panel 12 and the rear panel 13 cooperate with each other not only to form a waist region but also to function as an elastic belt to retain an absorbent structure 41 attached to the crotch panel 14 in a crotch region 4 of the wearer. The front panel 12 has an interior layer sheet 54 defining part of skin-facing surface corresponding to an interior surface of the diaper 10 and to an interior surface of the extended diaper also and an exterior layer sheet 56 defining an exterior surface, i.e., non-skin-facing surface of the extended diaper 10a. The exterior layer sheet 56 extends in the front-back direction Z in FIG. 2 from the interior layer sheet 54 and is folded back along an upper end edge 12a of the front panel 12 onto the side of an interior surface of the extended diaper 10a to overlap with this interior surface. Along the upper end edge 12a and a lower end edge 12b of the front panel 12, a plurality of first and second waist elastic members 57, 58 parallel extending in the transverse direction X are respectively secured under tension to the exterior layer sheet 56 with hot melt adhesive (not shown). The first waist elastic members 57 are interposed between the exterior layer sheet 56 folded back along the upper end edge 12a and overlapping with itself. The second waist elastic members 58 are interposed between an elongate cover sheet 59 partly forming the skin-facing surface and the exterior layer sheet 56.

The rear panel 13 has an interior layer sheet 64 defining the skin-facing surface and an exterior layer sheet 66 defining the non-skin-facing surface. An upper-end portion the exterior layer sheet 66 extends in the front-back direction Z from the interior layer sheet 64 and is folded back along an upper end edge 13a of the rear panel 13 onto the interior surface to overlap therewith. In end portions along the upper end edge 13a and a lower end edge 13b of the rear panel 13, respectively, a plurality of third and fourth waist elastic members 67, 68 extending parallel to the end edges 13a, 13b in the transverse direction X are arranged and secured to the outer layer sheet 66 with hot melt adhesive (not shown). The third waist elastics 67 are interposed between the exterior layer sheet 66 folded back along the upper end edge 13a and overlapping with itself. The fourth waist elastics 68 is interposed between a cover sheet 69 partly defining the skin-facing surface and the exterior layer sheet 66.

As material for these interior layer sheets 54, 64 and the exterior layer sheets 56, 66, nonwoven fabrics such as a spunbonded/meltblown/spunbonded nonwoven fabric (SMS nonwoven fabric) or a spunbonded nonwoven fabric each having a mass per unit area in a range of 15 to 30 g/m² or a plastic film having a thickness in a range of 10 to 50 μm may be used. To join the interior layer sheets 54, 64 to the exterior layer sheets 56, 66 and to join the exterior layer sheets 56, 66 to each other, hot melt adhesive may be used. In this regard, as will be apparent from FIG. 2, the second elastics 58 extend between the side edge portions 16 of the front panel 12 and the absorbent structure 41 on the crotch panel 14 so as to extend across the leg side flaps 42 but not to extend across the absorbent structure 41. The fourth waist elastics 68 extend between the side edge portions 17 of the rear panel 13 and the leg side flaps 42 not so as to extend across the absorbent structure 41 and the leg side flaps 42. Consequently, contraction of the fourth waist elastics 68 causes no contraction of the inner side regions 92 described later in more detail of the leg side flaps 42.

The front panel 12 and the rear panel 13 illustrated in FIG. 1 and arranged as described above may elastically fit the wearer's waist under contraction of the first, second, third and fourth waist elastics 57, 58, 67, 68.

The crotch panel 41 has the absorbent structure 41 located on a central region as viewed in the transverse direction X and the leg side flaps 42 extending in the front-back direction Z in FIG. 2 along the both side edges of the absorbent structure 41. The absorbent structure 41 has a front end portion 41a, a rear end portion 41b and an intermediate portion 41c. The front end portion 41a overlaps with the front panel 12 and is joined to the front panel 12 with hot melt adhesive (not shown). The front end portion 41a is partly covered with the folded back exterior layer sheet 56. The rear end portion 41b overlaps with the rear panel 13 and is joined thereto through the intermediary of hot melt adhesive (not shown) and partly interposed between the exterior layer sheet 66 and the interior layer sheet 64 and joined to these two sheets 66, 64 with hot melt adhesive (not shown). Each of the leg side flaps 42 of the crotch panel 14 is dimensioned in the front-back direction Z to be smaller than that of the absorbent structure 41 and has a front end portion 42a joined to the cover sheet 59 in the front panel 12 with hot melt adhesive (not shown) and a rear end portion 42b joined to the cover sheet 69 in the rear panel 13 with hot melt adhesive (not shown).

The absorbent structure 41 is constituted of an absorbent body 73 including an absorbent core 71 formed of, for example, fluff pulp or a mixture of fluff pulp and superabsorbent polymer particles widely used in the relevant technical field and a liquid-permeable covering sheet 72 formed of tissue paper or nonwoven fabrics, a liquid-permeable top sheet 74 adapted to cover at least upper surface, i.e., the skin-facing surface of the absorbent body 73 and a back sheet 76 formed of liquid-impermeable plastic films to cover a bottom surface of the absorbent body 73. An exterior sheet 79 (see FIGS. 1 and 3) formed of nonwoven fabrics is joined on the outer surface of the back sheet 76 with hot melt adhesive (not shown) so that the exterior surface of the crotch panel 14 may have a fabric-like texture.

Each of the leg side flaps 42 is formed from a pair of overlapping sheets 81, for example, a pair of water repellent nonwoven fabric sheets formed of thermoplastic synthetic fibers between which a plurality of thread-like leg elastics 82 are interposed, and has an outer side edge 83 and an inner side edge 84. The inner side edge 84 and a narrow region 86 extending along the inner side edge 84 and having a width dimension in a range of 2 to 5 mm are secured to the bottom surface of the absorbent body 73 and the back sheet 76 with hot melt adhesive (not sown) to define a proximal edge 87 of the leg side flap 42. The outer side edge 83 defines a distal edge 88 of the leg side flap 42. The leg side flap 42 has, as viewed in the transverse direction X, the outer side region 91 including a plurality of the leg elastic members 82 and the inner side region 92 including none of the leg elastic members 82. In the outer side region 91, the leg elastic members 82 extend from the front end portion 42a to the rear end portion 42b of the leg side flap 42 under tension and in parallel and are joined to at least one of a pair of the overlapping sheets 81 with hot melt adhesive (not shown). With such arrangement, the outer side region 91 is elastically contractible in the front-back direction Z in FIG. 2 and, in the diaper 10 in the state as illustrated in FIG. 1, a number of gathers 93 are formed in the outer side region 91 under contraction. While the inner side region 92 may be constituted of a pair of the sheets 81, in the illustrated embodiment, nonwoven fabrics are used as material for the sheets 81 and liquid-impermeable plastic films 94, for example, a polyethylene film having a thickness in a range of 10 to 20 μm is interposed between these two nonwoven fabric sheets 81 to make the inner side region 92 liquid-impermeable. In this regard, the plastic film 94 is present only in the inner side region 92 to avoid a possibility that, if the plastic film 94 is present also in the outer side region 94, elastic contraction required for the outer side region 91 may be restricted by the presence of the plastic film 94.

Figure 4:
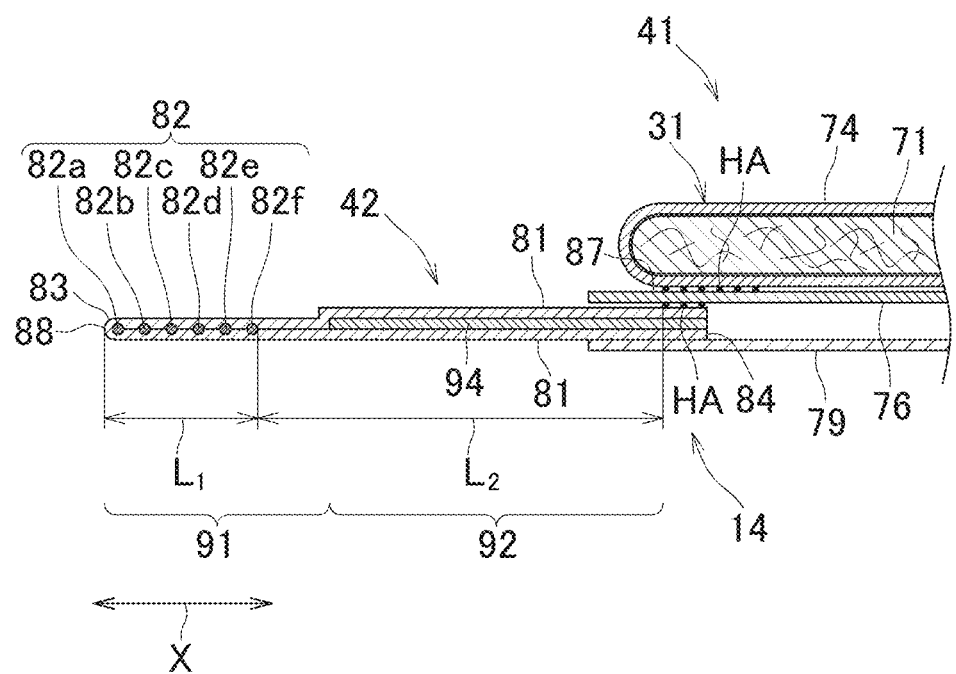
FIG. 4 is a sectional view taken along line IV-IV in FIG. 2.

FIG. 4 is a sectional view taken along line IV-IV in FIG. 2 and the line IV-IV is in coincidence with the transverse center line Q. The transverse center line Q is in coincidence also with a line extending in the transverse direction X along the lowest region 70 of the crotch region 4. In FIG. 4, the leg side flaps 42 prepared separately of the absorbent structure 41 are joined at the respective proximal edges 87 to the absorbent structure 41 with hot melt adhesive HA. In this regard, the other regions of hot melt adhesive in FIG. 4 are not shown. A pair of sheets 81 defining each of the leg side flaps 42 are formed of a single nonwoven fabric sheet doubled up along the distal edge 88.

The outer side region 91 of the leg side flap 42 includes the outermost elastic member 82a located along the distal edge 88 and designated as a first elastic member in the present invention and inner side elastic members 82b-82f arranged between the outermost elastic member 82a and the inner side region 92 and designated as the second elastic member or the third elastic members in the present invention. The designation "the second elastic members" used herein means the leg elastic members arranged on the inner side of the outermost elastic member 82a and having the same stretch ratio as that of the first elastic member 82a and the designation "the third elastic" used herein means the leg side elastic members arranged on the inner side of the outermost elastic member 82a and having a stretch ratio higher than that of the outermost elastic member 82a. The third elastic members are preferably located rather in an inner side area in the outer side region 91. The inner side elastic member 82f in the inner side elastic members 82b-82f may be designated as the innermost elastic member. Such outer side region 91 includes lateral sub-regions extending in the transverse direction X across the lowest region 70 of the crotch panel 14, i.e., the lateral sub-regions extending along the transverse center line Q which extends across the lowest region 70 and each of these lateral sub-regions has a dimension $L_1$ in the transverse direction X preset to at least 10 mm. The dimension $L_1$ is the dimension from the distal edge 88 to the innermost elastic member in the outer side region 91, for example, to the inner side elastic member 82f. In this regard, the term "stretch ratio" used herein means a ratio $S_1/S_2$, specifically, a ratio of a length $S_1$ of the elastic member measured on a test piece prepared by cutting out from the leg side flap 42 so as to include one of the leg elastic at a moment that the sheet 81 has been pulled until the gather due to contraction of the elastic member disappears versus a length $S_2$ of the elastic member in natural but straightened state after having been detached from the test piece by immersing the test piece in toluene solution. In this regard, the lengths $S_1$, $S_2$ may be defined, respectively, by dimensions between the lines marked on the test piece or the elastic member, respectively. In addition, the term "extension force" used herein means a force required to extend the test piece including single leg elastic member from the length thereof in relaxed natural condition twice the length. To conduct the measurement of this extension force on the test piece, any one of Autograph AG-Xplus series or a like-quality tester may be used at a rate of extension (a rate of pulling) set to 100 m/min.

The inner side region 92 in the waist side flap 42 is the region having none of the leg elastic members 82 or the region including the elastic member having a stretch ratio lower than that of the outermost elastic member 82a. The inner side region 92 having the lateral sub-region extending in the transverse direction X across the lowest region 70 of the crotch panel 14 in which a dimension $L_2$ in the transverse direction X set to at least 10 mm. This dimension $L_2$ corresponds to the dimension from the proximal edge 87 to the innermost elastic member 82f arranged in the innermost sub-region of the outer side region 91, as illustrated.

According to the embodiment illustrated in FIG. 4, spandex having fineness in a range of 310 to 620 dtex may be used at a stretch ratio preset to a range of 2.0 to 3.0 as the leg elastic members 82. As material for the sheet 81, the sheet material widely known in the related technique field such as SMS nonwoven fabrics or spunbonded nonwoven fabrics each having a mass per unit area in a range of 15 to 30 g/m² may be used. FIG. 1 exemplarily illustrates the case in which the inner side elastic members 82b-82f being the same as the outermost elastic member 82 in thickness as well as in length are used at the same stretch ratio as that of the outermost elastic member 82a. As will be apparent from FIG. 1, in each of the lateral sub-regions extending in the transverse direction X across the lowest region 70 of the crotch region 4, the inner side region 92 of the leg side flap 42 positively stands up so as to intersect with an imaginary vertical line $Y_1$ parallel to a vertical line indicated by a double-headed arrow Y at a relatively small intersecting angle α. Meanwhile, the outer side region 91 in which the elastic members 82a-82f are in a contracted state extends in the transverse direction X so as to intersect with the vertical line $Y_1$ at a relatively large intersecting angle β. In this manner, the inner side region 92 positively rises in the longitudinal direction Y and the outer side region 91 extends in the transverse direction X from the inner side region 92. Compared to the case in which the leg side flaps 42 as a whole, i.e., both the outer side regions 91 and the inner side regions 92 positively rises, the leg openings 23 formed in the above-mentioned manner according to this embodiment make it possible to maintain the leg openings in sufficiently opened condition. In consequence, the leg openings 23 are visually recognizable and easily targetable through the waist opening for a mother intending to put the diaper 10 on her baby's body. Furthermore, operation of passing the baby's legs through the leg openings 23 is facilitated. This operation is facilitated not only for the reason that the leg openings are maintained in sufficiently opened condition but also for the other reason relating to the particular arrangement of the leg side flaps 42. Specifically, if each of the leg side flaps 42 includes the regions defining walls which may rise and catch the baby's toe when the mother intends to pass her baby's legs through the leg openings 23, such regions in question are only the inner side regions 92. However, compared to the case in which both the inner side regions 93 and the outer side regions 91 positively rise in the longitudinal direction Y, the walls are sufficiently low to facilitate the mother's handling.

Furthermore, as will be apparent from FIG. 1, the distal edges 88 and the vicinity thereof rather behave to extend outward in the transverse direction X than upward in the longitudinal direction Y and such behavior facilitates the distal edges 88 and the vicinity thereof to extend downward along the legs in the course of passing the legs through the leg openings 23. Consequently, the entirety of the outer side regions 91 as viewed in the transverse direction X extend downward and smoothly come in close contact around the respective legs at a desired fit. If the leg side flaps 42 as a whole extend upward, the leg side flaps 42 as a whole will remain in extending upward even after the diaper 10 has been put on the baby's body so as to intersect with the vertical line $Y_1$ at a relatively small intersecting angle and, as the case may be, an exterior surface of a portion of one or both leg side flaps 42 will come in contact around the baby's legs, causing a possibility that the bodily-fluids such as urine leak may occur around the baby's legs. Considering such possibility, after having put the diaper 10 on the baby's body, it will be required for the mother to insert her hand(s) from the outside of the diaper 10 into the inside of the leg openings 23 and to force the portion in question to extend downward. In contrast, the diaper 10 according to the present invention assures that the respective outer side regions 91 are kept in close contact around the baby's legs at a desired fit to prevent leakage of the bodily-fluids which may occur around the legs without any troublesome posterior handling required for the mother.

To the function of the leg side flaps 42 as has been described above, a manner in which the leg side flaps 42 are attached to the rear panel 13 also contributes. Specifically, referring to FIG. 2, the fourth elastic members 68 for the rear panel 13 extend so as to intersect with the leg elastic members 82 arranged in the outer side regions 91 of the leg side flaps 42 but extend not to the inner side regions 92. With such arrangement, the dimension $L_2$ in the transverse direction X of the inner side regions 92 is not shortened even under contraction of the fourth waist elastic members 68 and the inner side regions 92 are apt to intersect with the vertical lines $Y_1$ indicated in FIG. 1 at a relatively large intersecting angle in the vicinity of the lowest region 70 of the crotch region 4. In this regard, the vertical lines $Y_1$ in FIG. 1 is defined as will be described as follows: an imaginary line X1 connecting top portions 10a of the side edge portions 16, 17 respectively opposite in the transverse direction X along which the front and rear panels 12, 13 are joined to each other may be horizontalized to be put approximately in coincidence with a double-headed arrow mark X. The vertical line $Y_1$ in FIG. 1 is the vertical line being orthogonal to such horizontal imaginary line X1 or another vertical line being orthogonal to such vertical line.

Figure 5:
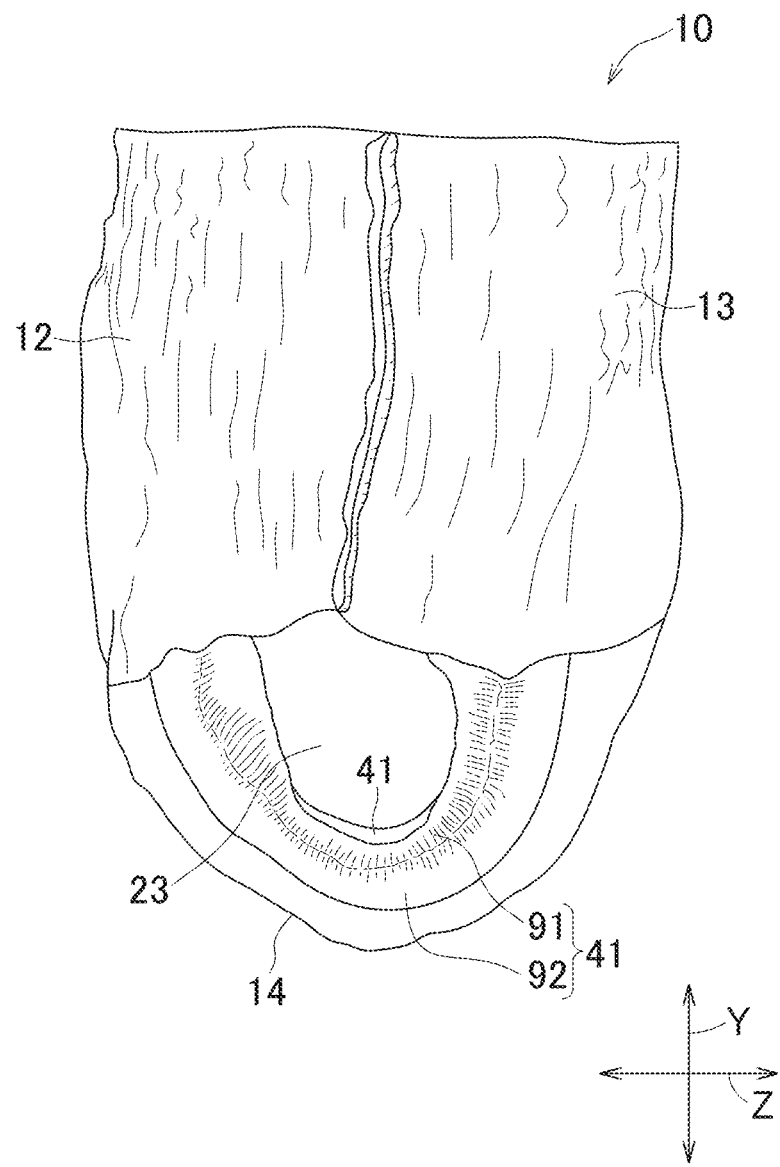
FIG. 5 is a side view of the diaper illustrated in FIG. 1.

FIG. 5 is a side view of the diaper 10 in FIG. 1, illustrating one of the leg openings 23 observed at a horizontal visual angle. As will be understood from FIG. 5, the outer side region 91 of the leg side flap 42 functions to outspread the leg opening 23.

Figure 6:
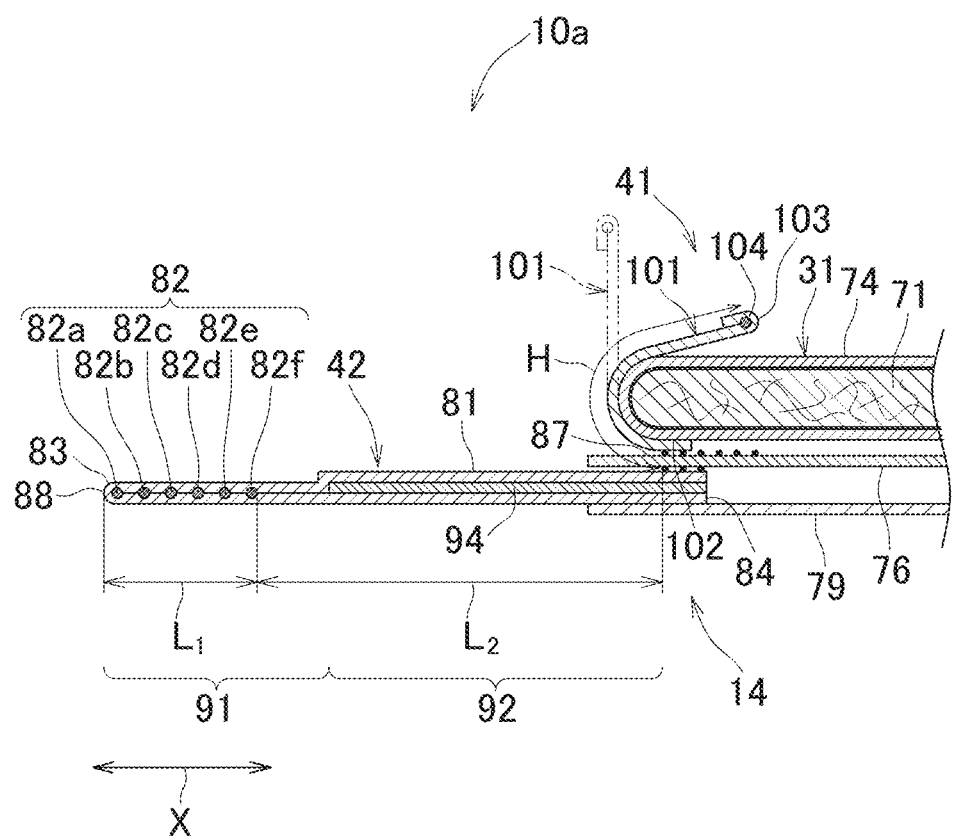
FIG. 6 is a view similar to FIG. 4, illustrating another embodiment.

FIG. 6 is a view similar to FIG. 4, illustrating another embodiment. In the extended diaper 10a illustrated in FIG. 6, leakage barrier cuffs 101 extending in the front-back direction Z are formed along the side edges of the absorbent structure 41. Each of the leakage barrier cuffs 101 is widely known in the relevant technical field and includes a base edge portion 102 joined to the leg side flap 42 in the vicinity of the proximal edge 87 and extending in the front-back direction Z and a free edge portion 103 extending in the front-back direction Z in parallel to the base edge portion 102 and provided with an elastic member 104 attached thereto under tension. While a portion extending between the base edge portion 102 and the free edge portion 103 is illustrated as collapsing toward the longitudinal center line P (see FIG. 2) and overlapping the skin-facing surface of the absorbent structure 41, the free edge portion 103 rises on the absorbent structure 41 as indicated by an imaginary line under contraction of the elastic member 104 and functions as the leakage barrier cuff 101. Though not illustrated, at the front end portion and the rear end portion of the leakage barrier cuff 101, the free edge portion 103 collapses onto the skin-facing surface of the absorbent structure 41 and bonded thereto. Such leakage barrier cuff 101 has a height H defined by a distance between the base edge portion 102 and the free edge portion 103 on the center line Q (see FIG. 2) extending in the transverse direction X across the lowest region 70 and this distance H is preset not to surpass the dimension $L_2$ of the inner side region 92 of the leg side flap 42. The free edge portion 103 of such leakage barrier cuff 101 has its height dimension being too small to be visually observed in the state as illustrated by FIG. 5 and there is no possibility that the baby's toe may be readily caught by the leakage barrier cuff 101, ensuring the convenience for putting the diaper 10 on the baby's body. In addition, the base edge portion 102 of the leakage barrier cuff 101 may be attached so as to overlap the proximal edge 87 or attached contiguously to the proximal edge 87 to assure that, even when the free edge portion 103 rises as indicated by an imaginary line under contraction of the elastic member 104, there is no possibility that the inner side region 92 of the leg side flap 42 may move upward together with the free edge portion 103 and positively rise from the proximal edge 87. In this manner, when the mother intends to pass the baby's legs through the leg openings 23, the baby's toe or toes may not be caught by the inner side regions 92 owing the presence of the leakage barrier cuffs 101.

Figure 7:
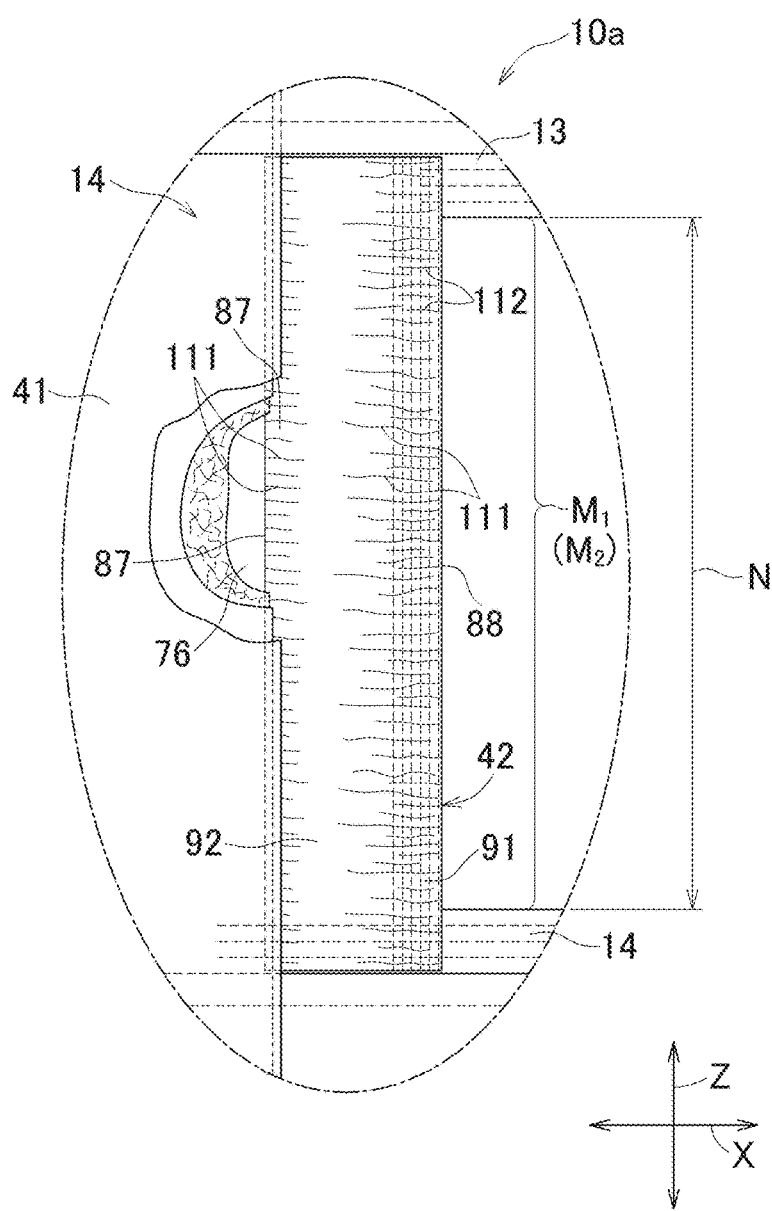
FIG. 7 is a partial view of the diaper according to still another embodiment.

FIG. 7 is a partially enlarged view of FIG. 2 to illustrate still another embodiment. In the crotch panel 14 illustrated in FIG. 7, a plurality of the proximal edge 87 of the leg side flap 42 formed with a number of gathers 111 parallel arranged in the transverse direction X, in other words, in the width direction of the leg side flap 42 is attached to the back sheet 76 and/or the exterior layer sheet 79 with hot melt adhesive (not shown). The gathers 111 are formed also in a region between the proximal edge 87 and the distal edge 88. In addition, the outer side region 91 also is formed with gathers 112 under contraction of the leg elastic members 82. In this regard, it is difficult in the real diaper 10 to visually distinguish the gathers 111 and the gathers 112 from each other. An apparent dimension M1 of such leg side flap 42 between the front panel 12 and the rear panel 13 is the same to a dimension N of the absorbent structure 41 as long as viewed in FIG. 7. However, a real dimension M2 of the leg side flap 42 as measured on the leg side flap 42 extended until the gathers 111, 112 disappear is a real length of the sheet 81 extending between the front and rear panels 12, 13 in FIG. 7 and a length thereof is larger than the dimension N. In the leg side flap 42 formed in this manner, an elastic contraction of the outer side region 91 is not restricted or negligibly restricted by the absorbent structure 41, allowing the outer side region 91 to contract with no significant restriction. In consequence, it is possible for the outer side region 91 in which the leg elastic members 82, for example, the leg elastic members 82 exemplarily illustrated in FIG. 4, more specifically, all the elastic members 82a-82f are uniform to extend approximately in parallel to the imaginary line X1 or at a small angle of obliquity to the imaginary line X1. The leg openings 23 including such outer side regions 91 ensure sufficient sizes to make it easy to pass the baby's legs therethrough.

By the way, a method of attaching such leg side flaps 42 to the absorbent structure 41 will be exemplarily described hereunder. Feeding a first web as a continuum of the sheet 81 forming the leg side flaps 42 in a machine direction, continuous elastic members as a continuum of the leg elastic members stretched at a desired stretch ratio is fed in the machine direction and secured to the first web at desired regions thereof to form first composite web. A pair of a first feed rollers having a relatively high circumferential velocity is set upstream in the machine direction and a pair of second feed rollers having a relatively low circumferential velocity is set downstream in the machine direction so that the first composite web may be formed with gathers corresponding to the gathers 111 upstream of the second feed rollers as the first composite web passes through these first and second feed rollers. The first web formed with the gathers in this manner is joined to a web as a continuum of the back sheet 76 with hot melt adhesive to form second composite web immediately after having passed through the a second feed rollers. After or before the second composite web is cut into a predetermined length the second composite web is joined to predetermined regions of the absorbent body 73 or the top sheet 74 or the back sheet 76 covering the absorbent body 73 intermittently fed in the machine direction with hot melt adhesive.

Figure 8:
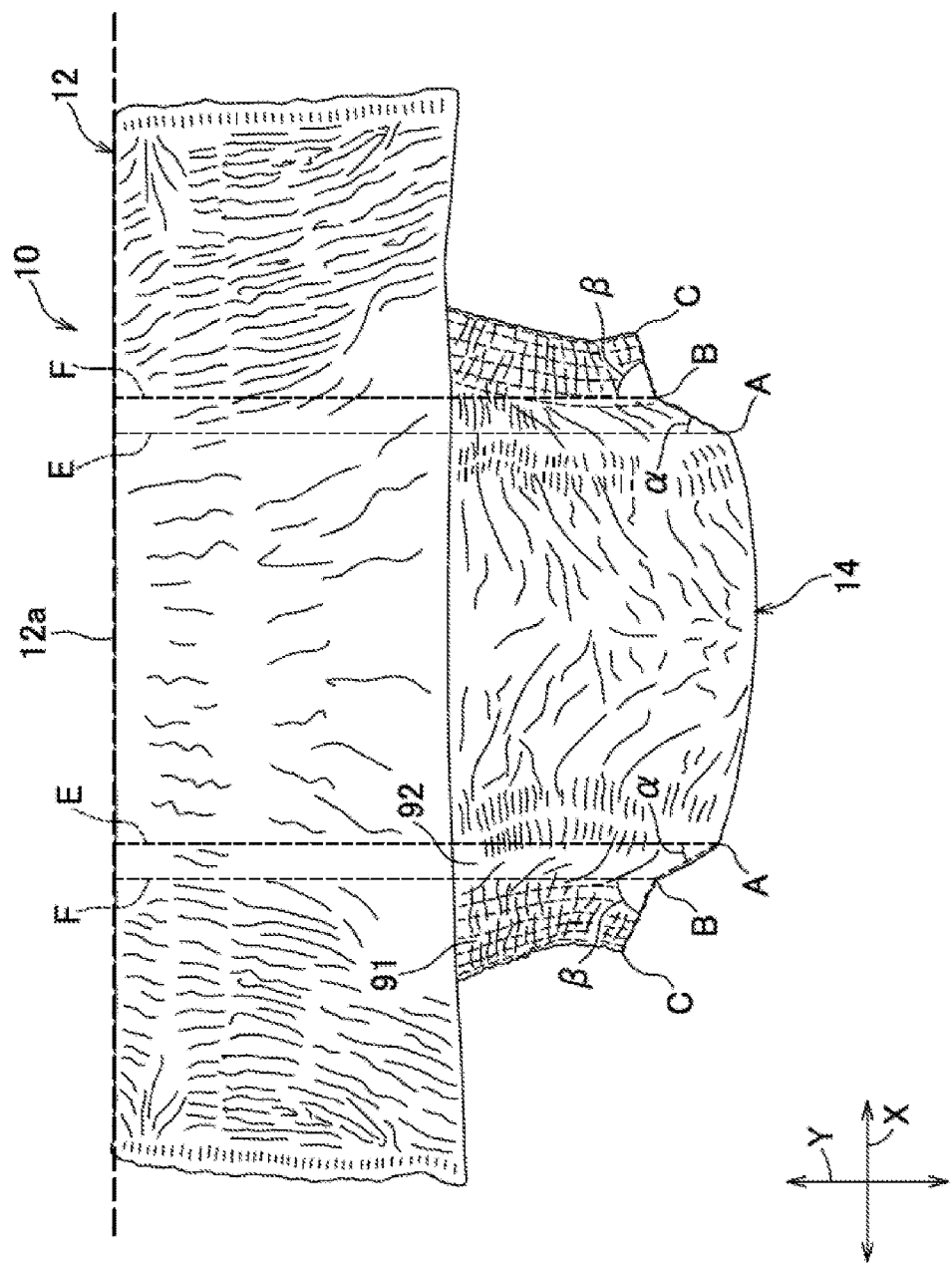
FIG. 8 is a photo indicating gradients in exterior region and interior region of leg side flaps.

FIG. 8 is a photo exemplarily showing a condition of the outer side regions 91 and the inner side regions 92 of the leg side flaps 42 as observed from the front of the diaper 10. In this regard, in the diaper shown in this photo, the front panel 12 has been extended together with the rear panel 13 until the gathers generated under contraction of the first and second waist elastic members 57, 58 disappear and the diaper 10 has been fixed to a flat plate (not shown) with the straightened upper end edge 12a of the front panel 12 being horizontalized. FIG. 8 may be designated also as a front elevational view of such diaper 10. The upper end edge 12a of this diaper 10 may be assumed as a horizontal line in coincidence with the imaginary line X1 in FIG. 1. In FIG. 8, the position of the proximal edge 87 is indicated by a point A, the position of the innermost elastic member 82f of the leg elastic members 82 in FIG. 4 defining a boundary between the outer side region 91 and the inner side region 92 of the leg side flap 42 is indicated by a point B and the position of the distal edge 88 of the leg side flap 42 is indicated by a point C. In addition, FIG. 8 indicates lines E, F passing the points A, B and orthogonal to the upper end edge 1a of the front panel 12. The lines E, F are parallel to each other and also to the vertical line $Y_1$ in FIG. 1. With use of such photo, it is possible to compare degrees of inclination of the outer side region 91 and the inner side region 92 of the leg side flap 42 in a quantitative manner.

Specifically, the inventors measured the intersecting angle α between the first straight line AB passing through the points A, B and the line E and the intersecting angle β between the second straight line BC passing through the points B, C and the line E. The measurement result suggested that, at least in the diaper 10 for baby, the intersecting angle α in a range of 15 to 40° and the intersecting angle β in a range of 50 to 90° ensure that the diaper 10 is smoothly put on the baby's body and the possibility of bodily fluid leakage is effectively restricted.

The disclosure relating to the present invention described hereinabove may be arranged at least as follows:

A disposable pull-on diaper having a longitudinal direction, a transverse direction and a front-back direction wherein side edge portions opposed to each other in the transverse direction of a front panel defining a front waist region are joined to side edge portions opposed to each other in the transverse direction of a rear panel defining a rear waist region to form an annular waist region and wherein front and rear end portions of a crotch panel extending in the front-back direction to define a crotch region are joined to the front waist region and the rear waist region, respectively, wherein:

the crotch panel includes an absorbent structure located in a central portion in the transverse direction thereof and a pair of leg side flaps extending along the absorbent structure on both sides in the transverse direction thereof; and the leg side flaps are formed of nonwoven fabric sheets extending in the transverse direction from the absorbent structure and a plurality of elastic members secured under tension to the respective nonwoven fabric sheets so as to extend parallel in the front-back direction, each of the leg side flaps has a proximal edge integrated with the absorbent structure and a distal edge defining each of side edges of the crotch panel, an area extending in the transverse direction between the proximal edge and the distal edge is divided into an outer side region including the distal edge and the leg elastic members and an inner side region including the proximal edge, one of the leg elastic members is secured to the distal edge, a dimension in the transverse direction between the outer side region and the inner side region is at least 10 mm in an area extending in the transverse direction across the lowest region in the longitudinal direction, the inner side region extends upward in the longitudinal direction from the proximal edge and the outer side region extends outward in the transverse direction from the proximal edge.

The disposable pull-on diaper according to the present invention disclosed in the above paragraph [0034] may include embodiments at least as described below and these embodiments may be adopted individually or in combination.

(1) In the crotch panel of the diaper extended in the transverse direction and set down so that the front panel may face upward, a first straight line connecting the leg elastic member lying on the innermost side of the outer side region to the proximal edge intersects with a vertical line orthogonal to a straight line extending along an upper end edge of the front panel at an angle α and a second straight line connecting the distal edge to the leg elastic member lying on the innermost side intersect with the vertical line at an angle β, wherein the angle α is in a range of 15 to 40° and the angle β is in a range of 50 to 90°.

(2) The outer side region is provided with at least one second elastic member having the same stretch ratio as that of the first elastic member.

(3) The outer side region is provided with at least one third elastic member having a stretch ratio larger than that of the first elastic member secured thereto on the inner side of the first elastic member.

(4) The outer side region is provided with at least one third elastic member having a stretch ratio larger than that of the first elastic member secured thereto on the inner side of the second elastic member.

(5) The interior surface of the crotch panel is formed with leakage barrier cuffs adapted to stand up toward the wearer's skin and each of the leakage barrier cuffs has a base end portion extending along the proximal edge and joined to at least one of the leg side flap and the absorbent structure and a free edge portion being elastically/contractible in parallel to the base end portion.

(6) In an area extending in the transverse direction across the lowest region of the crotch panel, a distance between the base end portion of the leakage barrier cuff and the free edge portion is not larger than a distance between the proximal edge and the outer side region in the leg side flap.

(7) The front panel, the rear panel and the crotch panel cooperate together to define leg openings and when the leg openings are observed from the outside at a horizontal viewing angle, the free edge portions of the respective leakage barrier cuffs are not visible inside the leg openings.

(8) The absorbent structure and the leg side flaps in the crotch region are separately prepared and may be joined to each other along the proximal edges of the leg side flaps to be integrated with each other and the proximal edges are formed with gathers parallel extending in the transverse direction when these proximal edges are joined to the absorbent structure.

REFERENCE SIGNS LIST 10 disposable pull-on diaper
12 front panel
12a upper end edge
13 rear panel
14 crotch panel
16 side edge portions
17 side edge portions
41 absorbent structure
42 leg side flaps
82 leg elastic members
82a first elastic member (outermost elastic member)
82f innermost elastic member
87 proximal edges
88 distal edges
91 outer side regions
92 inner side regions
101 leakage barrier cuffs
102 proximal edges
103 free edges
111 gather
E vertical line
F vertical line
H distance
$L_1$ dimension
$L_2$ distance, dimension
$Y_1$ vertical line
X transverse direction
Y longitudinal direction
Z front-back direction

The invention claimed is:

1. A disposable pull-on diaper, comprising:
a longitudinal direction, a transverse direction, and a front-back direction;
a front panel defining a front waist region and including front side edge portions opposed to each other in the transverse direction;
a rear panel defining a rear waist region and including rear side edge portions opposed to each other in the transverse direction; and
a crotch panel extending in the front-back direction and defining a crotch region,
wherein
the front side edge portions of the front panel are joined to the rear side edge portions of the rear panel to form an annular waist region,
the crotch panel includes
front and rear end portions joined to the front waist region and the rear waist region, respectively,
an absorbent structure located in a central portion of the crotch panel in the transverse direction,
a pair of leg side flaps extending along the absorbent structure on two sides of the crotch panel in the transverse direction, and formed of nonwoven fabric sheets extending in the transverse direction from the absorbent structure, and
a plurality of leg elastic members secured under tension to the respective nonwoven fabric sheets and extending parallel in the front-back direction,
each of the leg side flaps has
a proximal edge integrated with the absorbent structure, and a distal edge defining one of side edges of the crotch panel,
a region extending in the transverse direction between the proximal edge and the distal edge and divided into (i) an outer side region including the distal edge and the leg elastic members and (ii) an inner side region including the proximal edge,
the outer side region includes
a first leg elastic member among the plurality of leg elastic members, and
at least one of a second leg elastic member among the plurality of leg elastic members or a third leg elastic member among the plurality of leg elastic members,
the first leg elastic member is integrated with the distal edge,
the second leg elastic member has a same stretch ratio as the first leg elastic member,
the third leg elastic member has a higher stretch ratio than that of the first leg elastic member,
the inner side region includes no leg elastic members or has a leg elastic member having a lower stretch ratio than the first leg elastic member,
a dimension in the transverse direction between the outer side region and the inner side region is at least 10 mm in an area extending in the transverse direction across a lowest region in the longitudinal direction, and
in a state in which the crotch panel extends in the transverse direction and is set down to have the front panel facing upward, in the area extending in the transverse direction across the lowest region,
the inner side region extends upward in the longitudinal direction from the proximal edge, and
the outer side region extends outward in the transverse direction from the proximal edge.

2. The diaper according to claim 1 wherein, in the state in which the crotch panel extends in the transverse direction and is set down to have the front panel facing upward, in each of the leg side flaps,
a first straight line connecting an innermost leg elastic member among the plurality of leg elastic members in the outer side region to the proximal edge intersects with a vertical line orthogonal to a straight line extending along an upper end edge of the front panel at a first angle,
a second straight line connecting the distal edge to said innermost leg elastic member intersects with the vertical line at a second angle, and
the first angle is in a range of 15 to 40° and the second angle is in a range of 50 to 90°.

3. The diaper according to claim 1, wherein the third leg elastic member is disposed, in the transverse direction, inward from the first leg elastic member.

4. The diaper according to claim 1, wherein the third leg elastic member is disposed, in the transverse direction, inward from from the second leg elastic member.

5. The diaper according to claim 1, wherein
an interior surface of the crotch panel is formed with leakage barrier cuffs adapted to rise toward a wearer's skin, and
each of the leakage barrier cuffs has
a base end portion extending along the proximal edge of a corresponding one of the leg side flaps, and joined to at least one of (i) the corresponding leg side flap or (ii) the absorbent structure, and
a free edge portion elastically contractible and extending in parallel to the base end portion.

6. The diaper according to claim 5, wherein, in the area extending in the transverse direction across the lowest region of the crotch panel and in each of the leg side flaps,
a distance between the base end portion of the leakage barrier cuff and the free edge portion of the leakage barrier cuff is not larger than a distance between the proximal edge and the outer side region in the leg side flap.

7. The diaper according to claim 5, wherein
the front panel, the rear panel and the crotch panel cooperate together to define leg openings, and
when the leg openings are observed from an outer side of the leg openings at a horizontal viewing angle, the free edge portions of the respective leakage barrier cuffs are not visible inside the leg openings.

8. The diaper according to claim 1, wherein
the absorbent structure is joined to the leg side flaps in the crotch region along the proximal edges of the leg side flaps, and
the proximal edges are formed with gathers extending in the transverse direction.

9. The diaper according to claim 1, wherein, when the crotch panel is set down to have the front panel facing upward, in the area extending in the transverse direction across a lowest region of the crotch panel in the longitudinal direction,
the inner side region extends, from the proximal edge, upward in the longitudinal direction and outward in the transverse direction at a first angle relative to a vertical line orthogonal to a straight line extending along an upper end edge of the front panel,
the outer side region extends outward in the transverse direction from the inner side region at a second angle relative to the vertical line, and
the second angle is greater than the first angle.

10. A disposable pull-on diaper, comprising:
a longitudinal direction, a transverse direction, and a front-back direction;
a front panel defining a front waist region and including front side edge portions opposed to each other in the transverse direction;
a rear panel defining a rear waist region and including rear side edge portions opposed to each other in the transverse direction; and
a crotch panel extending in the front-back direction and defining a crotch region,
wherein
the front side edge portions of the front panel are joined to the rear side edge portions of the rear panel to form an annular waist region,
the crotch panel includes
front and rear end portions joined to the front waist region and the rear waist region, respectively,
an absorbent structure located in a central portion of the crotch panel in the transverse direction,
a pair of leg side flaps extending along the absorbent structure on two sides of the crotch panel in the transverse direction, and formed of nonwoven fabric sheets extending in the transverse direction from the absorbent structure, and
a plurality of leg elastic members secured under tension to the respective nonwoven fabric sheets and extending parallel in the front-back direction,
each of the leg side flaps has
a proximal edge integrated with the absorbent structure, and a distal edge defining one of side edges of the crotch panel,
a region extending in the transverse direction between the proximal edge and the distal edge and divided into (i) an outer side region including the distal edge and the leg elastic members and (ii) an inner side region including the proximal edge,
the outer side region includes a first leg elastic member among the plurality of leg elastic members and at least one of a second leg elastic member among the plurality of leg elastic members or a third leg elastic member among the plurality of leg elastic members,
the first leg elastic member is integrated with the distal edge,
the second leg elastic member has a same stretch ratio as the first leg elastic member,
the third leg elastic member has a higher stretch ratio than that of the first leg elastic member,
the inner side region does not include the plurality of leg elastic members or has a leg elastic member having a lower stretch ratio than the first leg elastic member, and
when the crotch panel is set down to have the front panel facing upward, in an area extending in the transverse direction across a lowest region of the crotch panel in the longitudinal direction,
each of the inner and outer side regions has a dimension of at least 10 mm in the transverse direction,
the inner side region extends upward in the longitudinal direction from the proximal edge, and
the outer side region extends outward in the transverse direction from the inner side region.

\* \* \* \* \*